United States Patent
Ufkes

(10) Patent No.: US 10,583,212 B2
(45) Date of Patent: Mar. 10, 2020

(54) PORTABLE UV-C DISINFECTION APPARATUS, METHOD, AND SYSTEM

(71) Applicant: UD Innovations, LLC, Sullivan's Island, SC (US)

(72) Inventor: Philip J. Ufkes, Sullivan's Island, SC (US)

(73) Assignee: UD Innovations, LLC, Sullivan's Island, SC (US)

( * ) Notice: Subject to any disclaimer, the term of this patent is extended or adjusted under 35 U.S.C. 154(b) by 120 days.

(21) Appl. No.: 15/869,444

(22) Filed: Jan. 12, 2018

(65) Prior Publication Data

US 2018/0193502 A1    Jul. 12, 2018

Related U.S. Application Data

(60) Provisional application No. 62/445,408, filed on Jan. 12, 2017.

(51) Int. Cl.
*A61L 2/10* (2006.01)
*A61L 2/28* (2006.01)
(Continued)

(52) U.S. Cl.
CPC .............. *A61L 2/10* (2013.01); *A61B 90/70* (2016.02); *A61L 2/24* (2013.01); *A61L 2/28* (2013.01)

(58) Field of Classification Search
CPC ..... A61L 2/10; A61L 2/28; A61L 2/24; A61L 2202/25; A61B 90/70
See application file for complete search history.

(56) References Cited

U.S. PATENT DOCUMENTS 5,628,303 A    5/1997    Ahmady et al.
6,078,425 A    6/2000    Wolfe et al.
(Continued)

FOREIGN PATENT DOCUMENTS

DE    202014001022 U1    5/2015
WO    2016069701 A1    5/2016

OTHER PUBLICATIONS

Indigo Clean, 2016 (Year: 2016).*
(Continued)

*Primary Examiner* — Sean E Conley
*Assistant Examiner* — Brendan A Hensel
(74) *Attorney, Agent, or Firm* — Gregory Finch; Finch Paolino, LLC

(57) ABSTRACT

A portable UV-C disinfection apparatus, method, and system for ultraviolet germicidal irradiation. UV-C emitters may be coupled to an array housing having a planar array surface in a vertical configuration. UV-C sensors are configured to measure the amount of UV-C light or near UV-C light from a target surface. A controller may be configured to engage with the UV-C sensors to determine the amount of UV-C radiation collected by the UV-C sensors. The controller includes instructions stored on a memory according to the amount of UV-C radiation collected corresponding to an effective kill-dose for surface disinfection. The improved apparatus, method, and system reduces exposure time by varying the intensity and wavelength of the UV-C administered, while concurrently reducing UV overexposure to surfaces by administering radiation through a rotational zonal application.

15 Claims, 13 Drawing Sheets

(51) Int. Cl.
*A61L 2/24* (2006.01)
*A61B 90/70* (2016.01)

(56) References Cited

U.S. PATENT DOCUMENTS

| | | |
|---|---|---|
| 6,656,424 B1 | 12/2003 | Deal |
| 6,911,177 B2 | 6/2005 | Deal |
| 7,175,806 B2 | 2/2007 | Deal et al. |
| 7,459,694 B2 | 12/2008 | Scheir et al. |
| 7,754,156 B2 | 7/2010 | Hyde et al. |
| 7,763,212 B2 | 7/2010 | McEllen |
| 7,829,016 B2 | 11/2010 | Deal et al. |
| 8,067,750 B2 | 11/2011 | Deal |
| 8,114,342 B2 | 2/2012 | Jung et al. |
| 8,178,042 B2 | 5/2012 | Jung et al. |
| 8,226,887 B2 | 7/2012 | Harmon et al. |
| 8,398,264 B2 | 3/2013 | Anderson et al. |
| 8,455,832 B2 * | 6/2013 | Statham ............ G01J 1/32 250/354.1 |
| 8,575,567 B2 | 11/2013 | Lyslo et al. |
| 8,584,612 B2 | 11/2013 | Hart et al. |
| 8,859,994 B2 | 10/2014 | Deal |
| 8,932,535 B2 | 1/2015 | Hyde et al. |
| 9,039,966 B2 | 5/2015 | Anderson et al. |
| 9,205,162 B2 | 12/2015 | Deal et al. |
| 9,358,313 B2 | 6/2016 | Deal |
| 9,370,600 B1 | 6/2016 | DuPuis et al. |
| 9,657,177 B1 | 5/2017 | Pringle et al. |
| 2002/0192361 A1 | 12/2002 | Chang et al. |
| 2006/0215257 A1 | 9/2006 | Morrow et al. |
| 2007/0023710 A1 | 2/2007 | Tom et al. |
| 2008/0019861 A1 | 1/2008 | Silderhuis |
| 2010/0060194 A1 | 3/2010 | Furry et al. |
| 2012/0121457 A1 | 5/2012 | Farren |
| 2012/0126134 A1 * | 5/2012 | Deal ............ A61L 2/10 250/372 |
| 2012/0308784 A1 | 12/2012 | Chen |
| 2013/0330235 A1 | 12/2013 | Stibich et al. |
| 2014/0044590 A1 | 2/2014 | Trapani |
| 2014/0131595 A1 | 5/2014 | Nathan et al. |
| 2015/0062893 A1 | 3/2015 | Lynn et al. |
| 2015/0086420 A1 | 3/2015 | Trapani |
| 2015/0217012 A1 * | 8/2015 | Garner ............ A61L 2/10 422/24 |
| 2015/0250914 A1 | 9/2015 | Aeifin et al. |
| 2016/0046839 A1 | 2/2016 | Maruno et al. |
| 2016/0058020 A1 | 3/2016 | Shur et al. |
| 2016/0067365 A1 | 3/2016 | Ma et al. |
| 2016/0219859 A1 | 8/2016 | Deal |
| 2016/0271281 A1 | 9/2016 | Clynne et al. |
| 2016/0271803 A1 | 9/2016 | Stewart |
| 2016/0296649 A1 | 10/2016 | Ramanand et al. |
| 2016/0375166 A1 | 12/2016 | Kreitenberg |

OTHER PUBLICATIONS

Goldwasser (Year: 2011).*
Indigo-Clean. 3 pages. Accessed online Jan. 11, 2018 at https://Kenall.com/Indigo-Clean. Kenall, Kenosha, WI.
International search report, International application No. PCT/US2018/016666. dated Jun. 8, 2018. ISA/US, Alexandria, VA.
Rutala, W. et al., "Rapid Hospital Room Decontamination Using Ultraviolet (UV) Light with a Nanostructured UV-Reflective Wall Coating." Infection Control and Hospital Epidemiology. vol. 34, No. 5, pp. 527-529. May 2013. Cambridge University Press, Cambridge, UK.
International search report, International application No. PCT/US2018/013528. dated Mar. 28, 2018. ISA/US, Alexandria, VA.
International search report, International application No. PCT/US2018/013516. dated Apr. 4, 2018. ISA/US, Alexandria, VA.

* cited by examiner

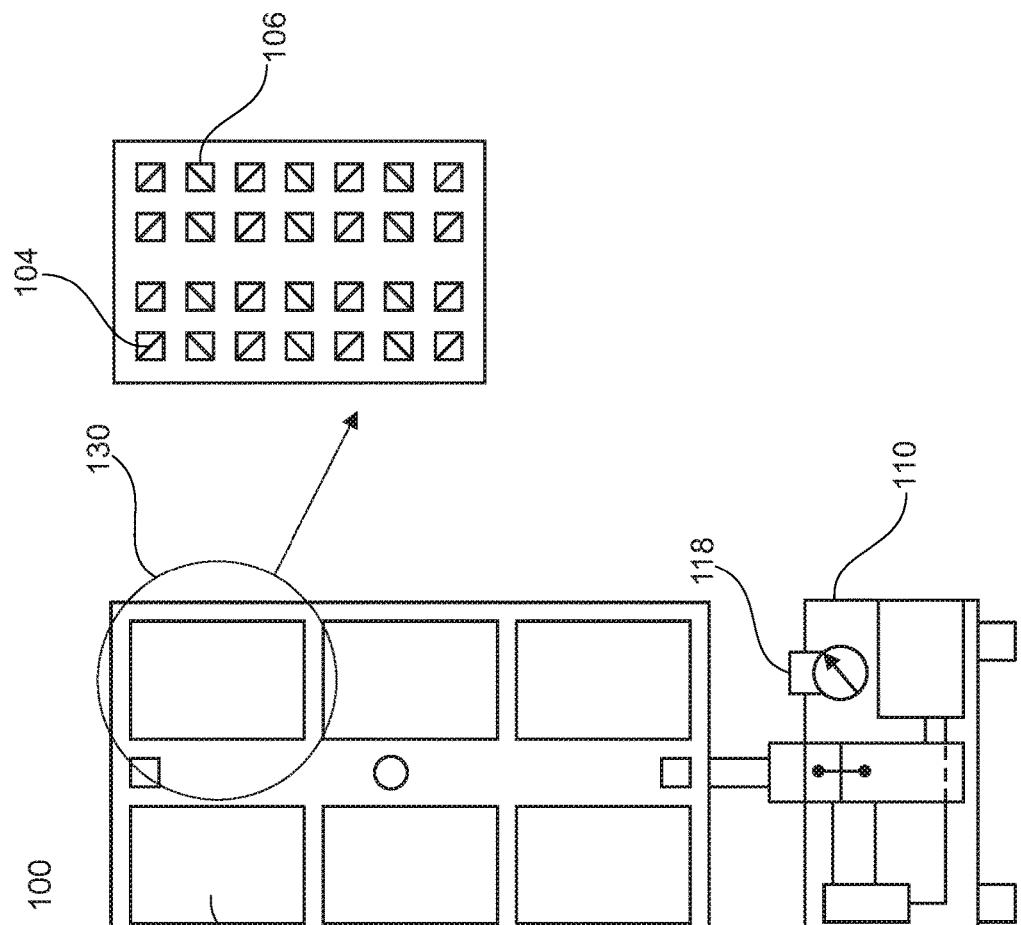
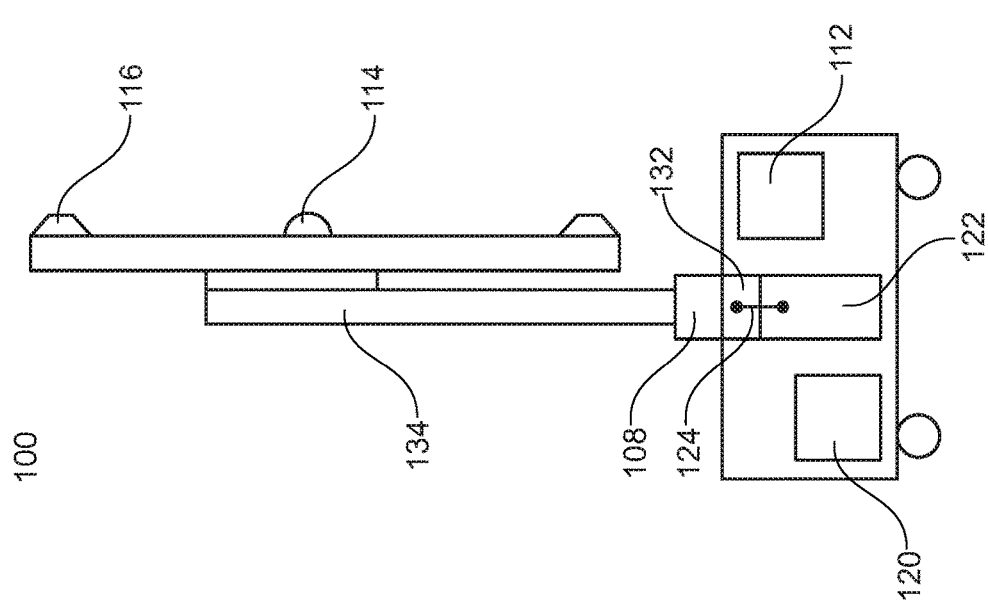
Fig. 1B
Fig. 1A

PORTABLE UV-C DISINFECTION APPARATUS, METHOD, AND SYSTEM

CROSS-REFERENCE TO RELATED APPLICATIONS

This application claims the benefit of U.S. Provisional Application Ser. No. 62/445,408, filed on Jan. 12, 2017 entitled "PORTABLE UV-C DISINFECTION APPARATUS, METHOD, AND SYSTEM", the disclosure of which is hereby incorporated in its entirety at least by reference.

BACKGROUND OF THE INVENTION

1. Field of the Invention

The present invention relates to methods and devices for bacterial, fungal and/or viral sterilization and disinfection, and is more particularly directed to a portable UV-C disinfection apparatus and system for ultraviolet germicidal irradiation.

2. Description of Related Art

Ultraviolet germicidal irradiation (UVGI) is a disinfection method that uses short-wavelength ultraviolet (UV-C) light to kill or inactivate microorganisms. One mechanism by which UV-C deactivates microorganisms is by destroying nucleic acids and disrupting their DNA, leaving them unable to perform vital cellular functions. The administration of UV-C radiation is becoming widely adopted by many hospitals as a more effective and reliable means of surface disinfection, as compared to the use of chemical cleaning agents alone. The effectiveness of germicidal UV-C irradiation depends on factors such as the length of time a microorganism is exposed to UV-C, the intensity and wavelength of the UV-C radiation, the presence of particles that can protect the microorganisms from UV, and a microorganism's ability to withstand UV-C during its exposure. In air and surface disinfection applications, the UV effectiveness is estimated by calculating the UV dose to be delivered to the microbial population. A method of calculating UV dose is as follows: UV dose $\mu Ws/cm^2$=UV intensity $\mu W/cm^2 \times$Exposure time (seconds).

Germicidal UV for disinfection is most typically generated by a mercury-vapor lamp. Low-pressure mercury vapor has a strong emission line at 254 nm, which is within the range of wavelengths that demonstrate strong disinfection effect. The optimal wavelengths for disinfection are close to 265 nm. UV-C LEDs use semiconductors to emit light between 255 nm-280 nm. The wavelength emission is tunable by adjusting the material of the semiconductor. The use of LEDs which emit a wavelength more precisely tuned to the maximal germicidal wavelength results in greater microbe deactivation per amp of power, maximization of microbial deactivation for the available, less ozone production, and less materials degradation. Although the germicidal properties of ultraviolet (UV) light have long been known, it is only comparatively recently that the antimicrobial properties of visible violet-blue 405 nm light have been discovered and used for environmental disinfection and infection control applications. A large body of scientific evidence is now available that provides underpinning knowledge of the 405 nm light-induced photodynamic inactivation process involved in the destruction of a wide range of prokaryotic and eukaryotic microbial species, including resistant forms such as bacterial and fungal spores. Violet-blue light, particularly 405 nm light, has significant antimicrobial properties against a wide range of bacterial and fungal pathogens and, although germicidal efficacy is lower than UV light, this limitation is offset by its facility for safe, continuous use in occupied environments.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

An object of the present disclosure is a portable UV-C disinfection apparatus comprising an array housing having a substantially planar array surface; a plurality of UV-C emitters coupled to the substantially planar array surface, the plurality of UV-C emitters being coupled to the substantially planar array surface in a substantially vertical configuration in relation to each other; at least one UV-C sensor coupled to the substantially planar array surface; at least one orientation sensor coupled to the array housing; a base housing, the base housing defining an interior portion; a motor being housed in the interior portion of the base housing, the array housing being coupled to a shaft of the motor at a bottom portion of the array housing; a controller being housed in the base housing, the controller being operably engaged with the motor, the at least one orientation sensor, the plurality of UV-C emitters, and the at least one UV-C sensor; and, a battery pack being housed in the base housing, the battery pack being operably engaged with the motor, the controller, the plurality of UV-C emitters, and the at least one UV-C sensor.

Another object of the present disclosure is a method for room disinfection using UV-C radiation comprising delivering, with a planar array of UV-C emitters, a beam of UV-C radiation to a first zone of a room; receiving, with at least one UV-C sensor, an amount of UV energy reflected from the first zone of the room; measuring, with a processor, a UV energy threshold for the at least one UV-C sensor; rotating, with an electric motor, the planar array of UV-C emitters to a second zone of the room in response to satisfying a UV energy threshold received by the at least one UV-C sensor; delivering, with the planar array of UV-C emitters, a beam of UV-C radiation to the second zone of the room; receiving, with the least one UV-C sensor, an amount of UV energy reflected from the second zone of the room; measuring, with the processor, a UV energy threshold in the second zone for the at least one UV-C sensor; rotating, with the electric motor, the planar array of UV-C emitters to an $N^{th}$ zone of the room in response to satisfying a UV energy threshold received by the at least one UV-C sensor.

Yet another object of the present disclosure is a system for room disinfection using UV-C radiation comprising at least one portable UV-C disinfection apparatus, the at least one portable UV-C disinfection apparatus comprising an array housing having a substantially planar array surface; a plurality of UV-C emitters coupled to the substantially planar array surface, the plurality of UV-C emitters being coupled to the substantially planar array surface in a substantially vertical configuration in relation to each other; at least one UV-C sensor coupled to the substantially planar array surface; at least one orientation sensor coupled to the array housing; a base housing, the base housing defining an interior portion; a motor being housed in the interior portion of the base housing, the array housing being coupled to a shaft of the motor at a bottom portion of the array housing; a controller being housed in the base housing, the controller being operably engaged with the motor, the at least one orientation sensor, the plurality of UV-C emitters, and the at least one UV-C sensor; a battery pack being housed in the base housing, the battery pack being operably engaged with the motor, the controller, the plurality of UV-C emitters, and the at least one UV-C sensor; a remote interface, the system interface being communicably engaged with the controller of the at least one portable UV-C disinfection apparatus; and, a database, the database being communicably engaged with the controller of the at least one portable UV-C disinfection apparatus and the system interface.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF THE SEVERAL VIEWS OF THE DRAWINGS

The above and other objects, features and advantages of the present disclosure will be more apparent from the following detailed description taken in conjunction with the accompanying drawings, in which:

FIG. 1A is a side view of a portable UV-C disinfection apparatus, according to an embodiment;

FIG. 113 is a front perspective view of a portable UV-C disinfection apparatus, according to an embodiment;

DETAILED DESCRIPTION OF THE INVENTION

Figure 1C:
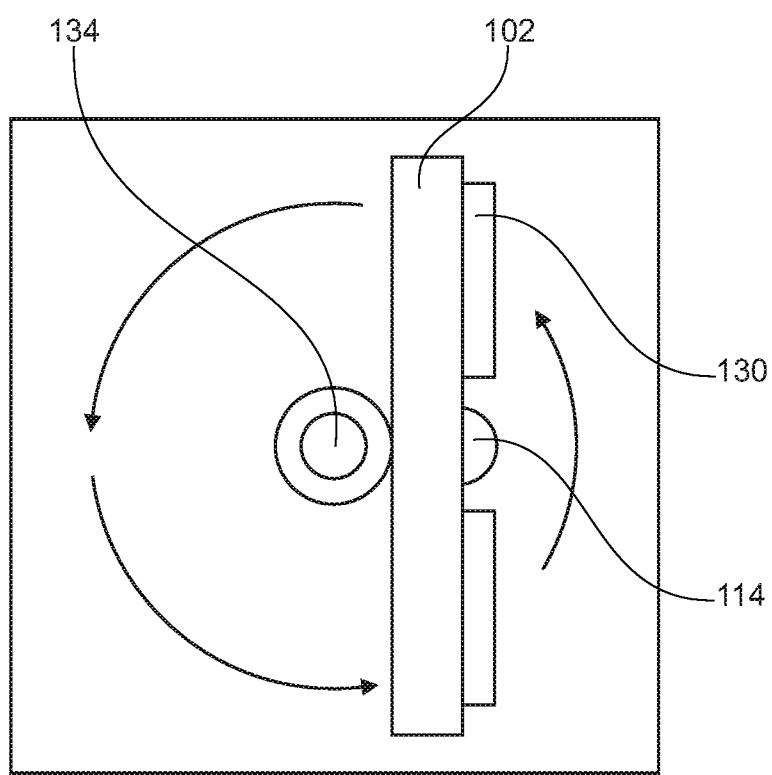
FIG. 1C is a top down view of a portable UV-C disinfection apparatus, according to an embodiment.

Exemplary embodiments are described herein to provide a detailed description of the present disclosure. Variations of these embodiments will be apparent to those of skill in the art. Moreover, certain terminology is used in the following description for convenience only and is not limiting. For example, the words "right," "left," "top," "bottom," "upper," "lower," "inner" and "outer" designate directions in the drawings to which reference is made. The word "a" is defined to mean "at least one." The terminology includes the words above specifically mentioned, derivatives thereof, and words of similar import.

Embodiments of the present disclosure provide for a UV-C disinfection apparatus that reduces exposure time by varying the intensity and wavelength of the UV-C administered, while concurrently reducing UV overexposure to surfaces by administering radiation through a rotational zonal application.

Referring now to FIGS. 1A-1C, a diagrammatic representation of a portable UV-C disinfection apparatus 100 is shown. According to an embodiment, portable UV-C disinfection apparatus 100 is generally comprised of an array housing 102, one or more UV-C emitters 104, one or more near UV emitters 106, a slip ring 108, a base housing 110, a controller 112, one or more UV-C sensors 114, a ranging sensor 116, an orientation sensor 118, a battery pack 120, a motor 122, motor shaft 124, one or more emitter arrays 130, an encoder 132, and an array support 134. Array housing 102 is coupled to base housing 110 via array support 134, which is coupled to motor shaft 124. Slip ring 108 is operably coupled to array support 134 via motor shaft 124, and functions to provide electrical connections between the components in array housing 102 and battery pack 120, as well as functions as a system bus between the components in array housing 102 and controller 112. Slip ring 108 is operable to enable array support 134 to rotate in a continuous 360-degree rotation via motor shaft 124 while maintaining circuitry connections with battery pack 120 and controller 112. Array housing 102 may be constructed of rigid or flexible material, such as plastic, metal, metal alloy, and the like. Base housing 110 provides a stationary foundation for apparatus 100, and may comprise wheels for ease of transportation and positioning.

According to an embodiment, one or more UV-C emitters 104, one or more near UV emitters 106, UV-C sensor 114, and ranging sensor 116, are coupled to a face portion of the array housing 102. In an embodiment, UV-C emitters 104 and near UV emitters 106 are preferably UV-C and/or visible light LEDs. In an alternative embodiment, UV-C emitters 104 and near UV emitters 106 are electronic gas-discharge lamps including but not limited to low-pressure mercury-vapor lamps, high-pressure mercury vapor lamps, xenon lamps, mercury-xenon lamps, pulsed-xenon lamps, and deuterium lamps. In another embodiment, UV-C emitters 104 and near UV emitters 106 may be CFL lamps and halogen lamps. Emitters 104 and near UV emitters 106 may be distributed in a linear arrangement over a 48-inch or 24-inch planar surface. Emitters 104 and near UV emitters 106 may be distributed in groups defining an emitter array 130. The linear arrangement of UV-C emitters 104 and near UV emitters 106 direct UV-C radiation in a targeted beam, enabling higher intensity emission with less power consumption as compared to an omnidirectional bulb—thereby enabling power to be supplied by a battery source, such as battery pack 120. The higher intensity generated by focusing a beam of UV-C radiation using a linear array, rather than an omnidirectional transmission generated by a mercury-vapor bulb or a circular LED array, has the dual benefits of reducing exposure time in the dosage calculation and conserving energy. In a preferred embodiment, UV-C emitters 104 are calibrated to have a wavelength emission of 265 nm, and near UV emitters 106 are calibrated to have a wavelength emission of 405 nm (which falls on the visible light spectrum). However, both emitters may be calibrated to various wavelength emissions within a known range of wavelengths that demonstrate strong disinfection effect. UV-C sensor 114 is a closed loop sensor operable to measure the amount of UV-C light or near UV light reflected from the target surface back to UV-C sensor 114. UV-C sensor 114 may be a single sensor or an array of multiple sensors, and may be either integral to array housing 102 or distributed in a target room. UV-C sensor 114 may be a dual band sensor comprised of a single carrier operable to measure UV-C radiation wavelengths of about 265 nm and near UV of about 405 nm. UV-C sensor 114 is operably engaged with controller 112 to communicate the amount of UV-C radiation (single or dual band) collected by UV-C sensor 114. Controller 112 has a set of instructions stored thereon to measure a "kill dose" according to the amount of reflected UV-C radiation collected by UV-C sensor 114 and kill dose parameters stored in memory. Controller 112 may calibrate various kill dose thresholds depending on the specific disinfection application. For example, viruses may require a lower kill dose, while bacteria may require a higher kill dose, and spores may require yet a higher kill dose.

Controller 112 may operate in communication with ranging sensor 116 to more accurately measure a kill dose delivered from emitters 104 and near UV emitters 106. The UV-C energy collected by UV-C sensor 114 might not accurately represent the amount of UV-C energy reflected by the target surface due to the distance, or air gap, between the target surface and UV-C sensor 114. This is due to the fact that UV-C radiation loses intensity as a function of distance travelled; therefore, the measured reflected energy at UV-C sensor 114 is less than the energy actually reflected by the target surface by a function of the distance between the target surface and UV-C sensor 114. Ranging sensor 116 may be operably engaged with controller 112 to calculate an "air gap compensation" to virtually relocate UV-C sensor 114 to the nearest object. This can be accomplished mathematically by correcting for the reduction in UV-C energy as a function of distance, as well as other variables such as temperature and humidity. Ranging sensor 116 is operably engaged to detect the distance to the nearest object in the zone of each UV-C sensor 114. Ranging sensor 116 may be comprised of, for example, one or more sensors capable of detecting the presence and location of objects within the sensor range without physical contact, such as sonic ranging, scanning ranging, and/or visible or infrared-based light sensors. Controller 112 may adjust the kill dose threshold of reflected energy received by UV-C sensor 114 in accordance with the distance input defined by ranging sensor 116. In the absence of ranging sensor 116, controller 112 may enable a manual input by a user to define the desired air gap adjustment.

Controller 112 may be positioned within an interior portion of base housing 110 or array housing 102. Battery pack 120 may be positioned within an interior portion of base housing 110 and is operable to provide all components of portable UV-C disinfection apparatus 100. Orientation sensor 118 is coupled to an interior or exterior portion of array housing 102, and is operable to enable controller 112 to detect unit location, array orientation, and zone position of UV-C disinfection apparatus 100. Orientation sensor 118 may be comprised of one or more motion sensors, real-time clocks, RFID, GPS, accelerometers, magnetic compass, gyroscopes, piezoelectric sensors, piezoresistive sensors, and capacitive orientation-sensing components or any other suitable means or orientation and location functioning; or any combination thereof.

Figure 1D:
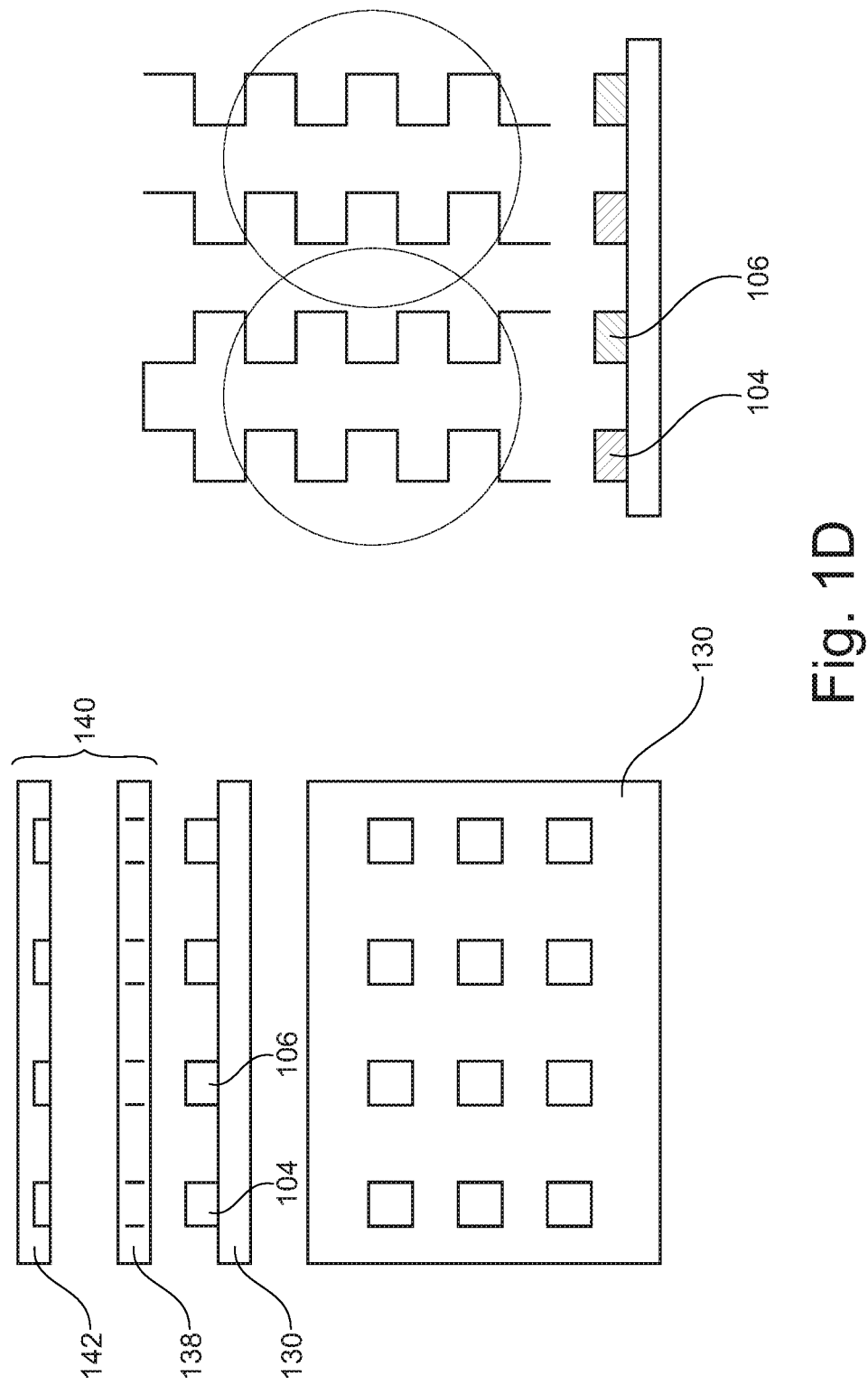
FIG. 1D is an exploded view of a lens assembly of a portable UV-C disinfection apparatus, according to an embodiment.

Referring now to FIG. 1D, emitter array 130 may further comprise a lens assembly 140. Lens assembly 140 may be comprised of a heat sink or reflector 138 and a lens 142. Lens assembly 140 functions to protect UV-C emitters 104 and near UV emitters 106 from damage, dissipate heat from emitters 104 and 106, and direct light in a desired angle (e.g. 120 degrees). Heat sink 138 functions to remove heat from UV-C emitters 104 and near UV emitters 106 to prevent overheating through conduction, and dissipate heat from heat sink 138 to the environment through convention and/or conduction. Heat sink 138 may be constructed of any suitable thermally conductive material. Lens 142 may be coupled to heat sink 138, and may function to protect UV-C emitters 104 and near UV emitters 106 from physical contact and environmental damage, such as dust accumulation. Lens 142 may be constructed from any UV-C transmittable material (for example, Acrylite); and, may be configured as a Fresnel lens such that lens 142 may be substantially planar in shape.

As discussed above, UV-C emitters 104 and near UV emitters 106 emit radiation at wavelengths of 265 nm and 405 nm respectively. Each wavelength displays its own kinetics of a kill curve for target microorganisms. It is anticipated that UV-C emitters 104 and near UV emitters 106 may pulse emission in-phase (i.e. emit light at the same time), or out of phase (i.e. emit light at opposite times), or operate independently, which may modify the kinetics of each wavelength's respective kill curve, such that a dual wavelength emission will reduce the overall time required to achieve a kill dose as compared to a single wavelength emission. Likewise, various modulation schema may be employed between UV-C emitters 104 and UV-C emitters 106 in order to optimize the kinetics of the kill curve for a given microorganism (e.g. viruses, bacteria, and spores), thereby reducing the amount of time required to achieve a kill dose for the target microorganism.

Figure 2:
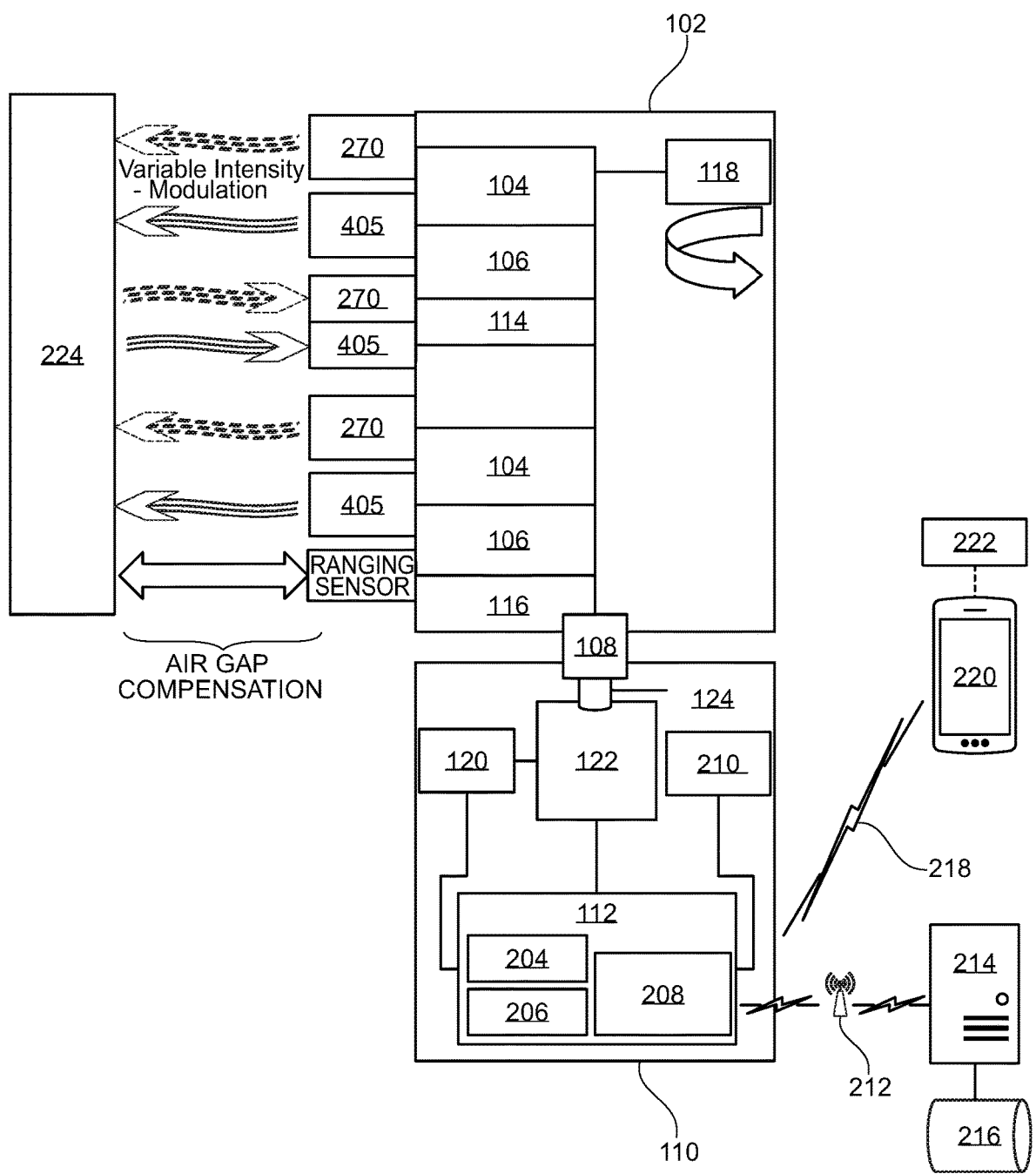
FIG. 2 is a system diagram of a portable UV-C disinfection system, according to an embodiment.

Referring now to FIG. 2, a system diagram of a portable UV-C disinfection system is shown. According to an embodiment, portable UV-C disinfection apparatus 100 administers UV-C radiation to a target zone via one or more UV-C emitters 104 and one or more near UV emitters 106. In a preferred embodiment, as mentioned above, UV-C emitters 104 are calibrated to emit short wave UV-C radiation at a wavelength of 265 nm, and near UV emitters 106 are calibrated to have a wavelength emission of 405 nm, or vice versa. Remote interface 220 is communicably engaged with controller 112 via a wireless communication interface, such as Bluetooth or WiFi. Remote interface 220 may be a tablet computer, smart phone, laptop computer, wireless I/O device, and the like. Remote interface 220 associates a room identifier 222 with a target room for disinfection. Remote interface 220 may include a user workflow configured to validate that a target room is prepped properly for disinfection and that all the steps in the disinfection workflow have been completed. A room identifier 222 may be a scanned barcode or RFID tag. Remote interface 220 communicates a request to begin a disinfection cycle to controller 112. Processor 204 processes the request to begin a disinfection cycle. Processor 204 executes instructions to orientation sensor 118 to determine a position and orientation in the target room. Processor 204 executes instructions for ranging sensor 116 to scan a Zone N 224 to determine the closest object in the target room. The data from orientation sensor 118 and ranging sensor 116 is stored in memory 206, along with room ID 222. Processor 204 executes instructions to measure air gap compensation to calibrate UV-C sensor 114 according to the data from ranging sensor 116. Processor 204 executes instructions to initiate UV-C emitters 104 and near UV emitters 106 to emit UV-C radiation to target Zone N 224. Radiation reflected from target Zone N 224 is reflected back to array housing 102 and is collected by UV-C sensor 114. UV-C sensor 114 sends UV dosage data to processor 204. Processor 204 executes instructions to measure a kill dose according to UV reflectivity data and air gap compensation variables. Once a threshold dosage value has been received by UV-C sensor 114, processor 204 executes instructions to discontinue UV-C emission by UV-C emitters 104 and near UV emitters 106 and rotate array housing to the next consecutive zone. Processor 204 executes instructions to store dosage data from Zone N 224 in memory. Processor 204 executes instructions to engage motor 122, thereby turning motor shaft 124 to rotate array housing 102 such that UV-C emitters 104 and near UV emitters 106 are oriented to the next consecutive zone. Slip ring 108 is the relay and the system bus between the components in array housing 102 and battery pack 120; and is the system bus between the components in array housing 102 and controller 112. Slip ring 108 enables array housing 102 to rotate in a 360-degree range of motion with motor shaft 124; however, the desired rotation may be calibrated to less than 360-degrees. Once array housing 102 has been rotated to the next zone, processor 204 executes the same instructions as those of Zone N 224 to deliver radiation to the next zone and measure a kill dose based on reflected radiation. This process is continued until UV-C emitters 104 and near UV emitters 106 have delivered a kill dose in a full 360-degree rotation (or the desired angular zones).

Processor 204 executes instructions to store dosage data from each zone in memory 208. The dosage data is time stamped, and communicated to hospital server 214 using wireless communication chip set 208 via hospital network 212. Hospital server 214 stores information retrieved from controller 112 in hospital database 216. This information can be utilized by hospital server 214 to determine the health of the hospital, as well as monitor the health and status of a facility wide deployment. Communication chip set 208 may be a LoRa chipset, and hospital network 212 may be configured as a low power wide area network (LPWAN) to reduce burden on the hospital's Wi-Fi network. LoRa is a wireless modulation for long-range, low-power, low-data-rate applications. LoRa is based on chirp spread spectrum modulation which maintains low-power characteristics and significantly increases communication range. LoRa commonly operates in the unlicensed frequency bands of 867-869 MHz and 902-928 MHz, although other frequency bands under 1000 MHz may be commonly utilized. Processor 204 may communicate a confirmation to remote interface 220 to confirm disinfection of the target room is complete.

Figure 3:
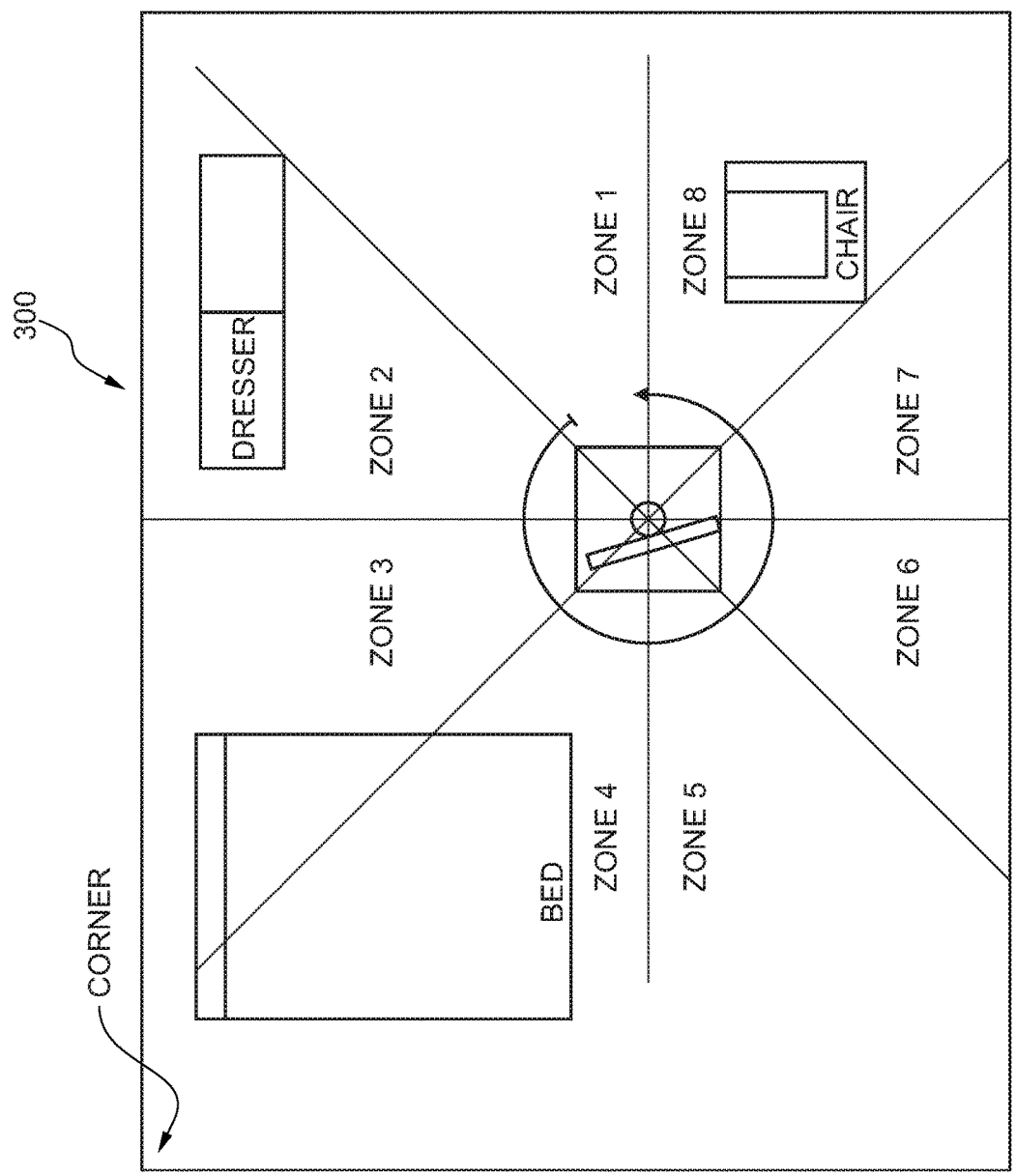
FIG. 3 is a schematic diagram of disinfection zones of a portable UV-C disinfection system, according to an embodiment.

Referring now to FIG. 3, a functional diagram of a portable UV-C disinfection system is shown. According to an embodiment, UV-C disinfection apparatus 100 is positioned in a target room for disinfection. UV-C disinfection apparatus 100 is operable to process a room identifier, orientation inside the room, and the desired zones for disinfection. The identity of the target room and the orientation of UV-C disinfection apparatus 100 within the target room may be determined by Real-Time Clock, RFID or other means to identify the room, GPS and other location methods, inertial navigation, magnetic navigation and other orientation methods. The UV-C sensors measure the UV-C energy reflected from the target zone. The ranging sensors measure the distance to the nearest object in the zone, and virtually relocate the UV-C sensors to the location of the nearest object to compensate for the air gap between the surface of the nearest object and the surface of the UV-C sensor. The UV-C emitters deliver UV-C light in a first zone, e.g. Zone 1. Due to the varying distance and reflectivity of zone surfaces and objects, the UV-C sensors may receive reflected energy at varying rates between zones. Reflective paints or reflective adhesive sheets may be used on hospital walls to increase the rate of UV-C reflectivity of the walls. Once a target area is disinfected, i.e. has received a kill dose, the array stores the zone dosage information and rotates the array to the next consecutive zone, e.g. Zone 2. Information regarding the orientation of objects in the zones and room location is saved in the memory of the UV-C disinfection apparatus. UV-C disinfection apparatus 100 may be programmed to exclude zones in certain spaces, e.g. "keep out zones." Likewise, UV-C disinfection apparatus 100 may be programmed to disinfect non-successive zones in a predetermined disinfection path. UV-C disinfection apparatus 100 delivers radiation in a predetermined path until all zones (in this illustration Zones 1-8) have received a kill dose, as measured by the reflected energy at the UV-C sensors. In a preferred embodiment, the area of each zone and intensity of UV-C emission is calculated such that UV-C disinfection apparatus 100 is operable to deliver a kill-dose to all desired zones by continuous rotation. Upon delivering a kill dose to all desired zones, the disinfection cycle is concluded and a confirmation is communicated to the remote interface and hospital server. The data collected during the disinfection cycle, such as air gap compensation, keep-out zones, disinfection path, and dosage allocation, is stored in the UV-C disinfection apparatus memory under a unique room identifier. This data may be acquired by a hospital server to monitor the health and status of a facility wide deployment.

Figure 4:
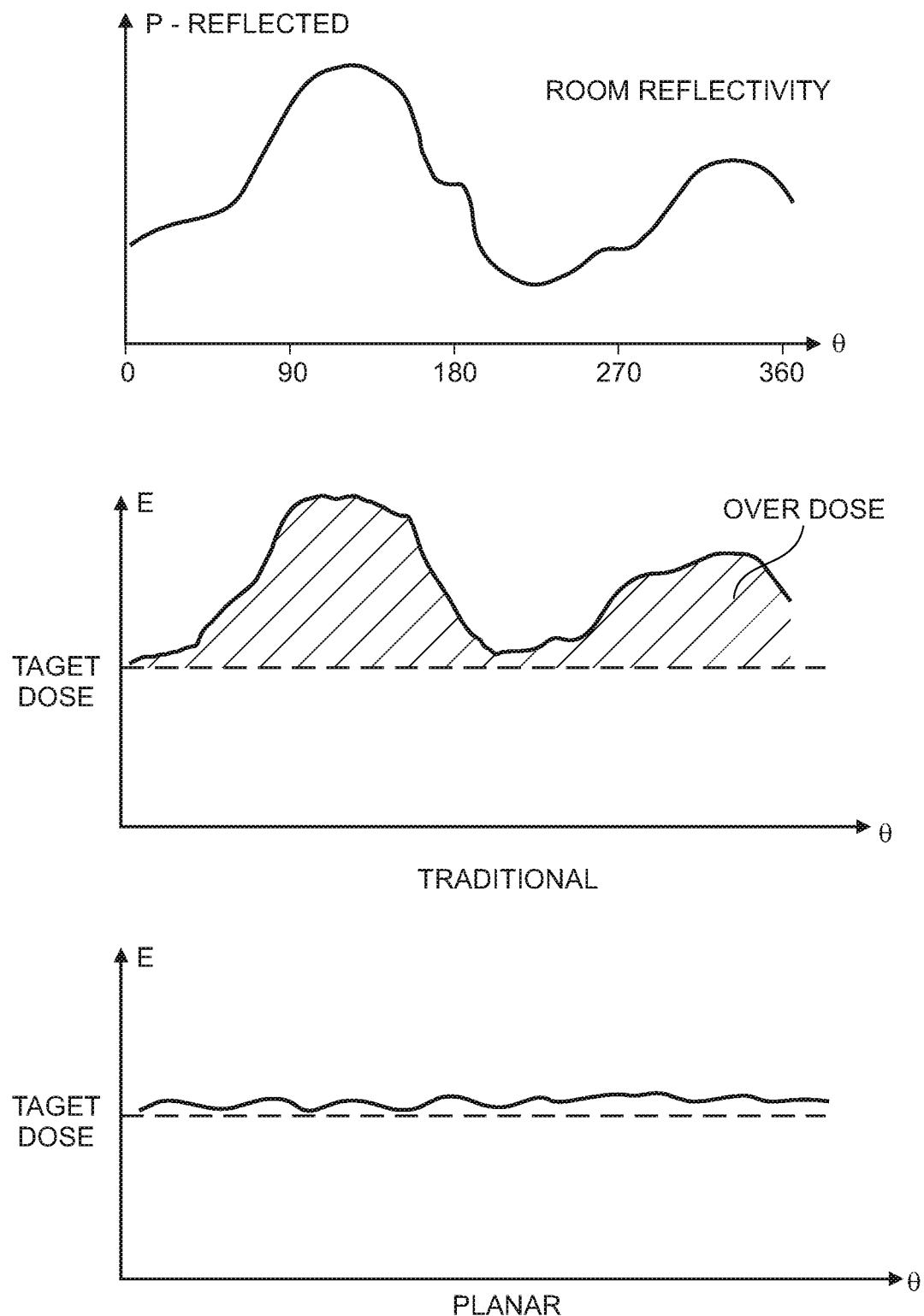
FIG. 4 is an illustration of UV-C emission plots comparing prior art solutions to embodiments of the present disclosure.

FIG. 4 further illustrates the concepts from FIG. 3; in particular, the ability of the present disclosure to solve the problem of over exposure of UV-C radiation during a UV-C disinfection process, as compared to the prior art. Prior art solutions emit UV-C radiation in an omnidirectional pattern. A kill dose is measured when a threshold amount of reflected energy is measured at the UV-C sensor on the UV-C disinfection apparatus. Since a target room exhibits different rates of reflectivity at different locations within the room, a UV-C disinfection apparatus that administers radiation in an omnidirectional pattern is reliant on the least reflective surface in the room to measure a kill dose at the UV-C sensor. Embodiments of the present disclosure, as discussed above, administer radiation and measure reflected energy on a per zone basis; thereby delivering only the necessary amount of radiation required for a particular zone, and not more. This dramatically reduces the overall amount of excess radiation delivered to the target room, as embodiments of the present disclosure enable emission of radiation and measurement of reflected energy specifically in the target zone.

Figure 5:
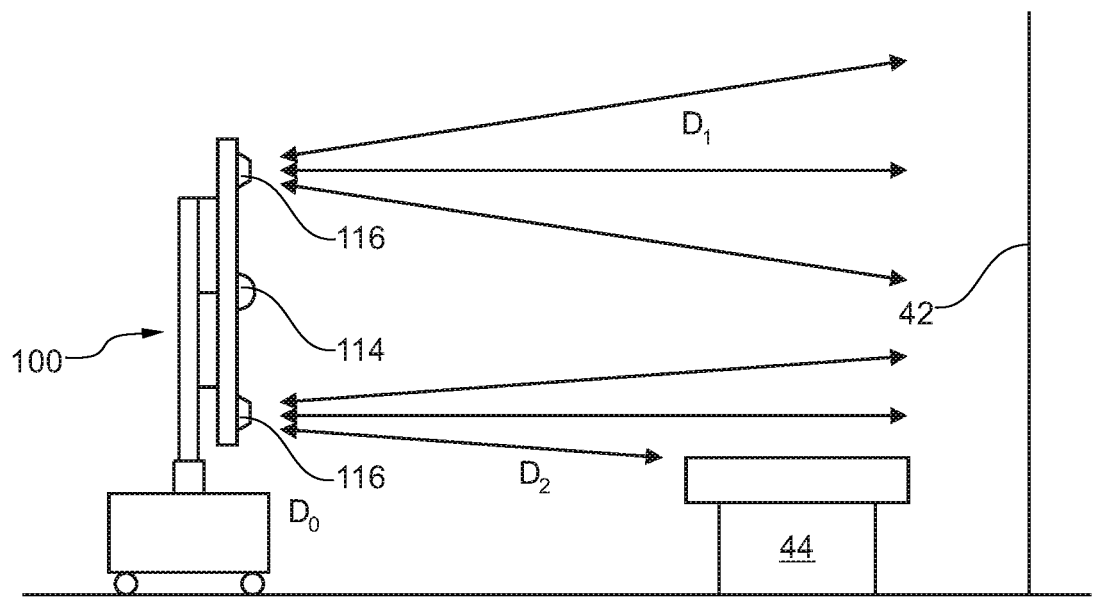
FIG. 5 is an illustration of an air gap compensation calculation, according to an embodiment.
Figure 5:
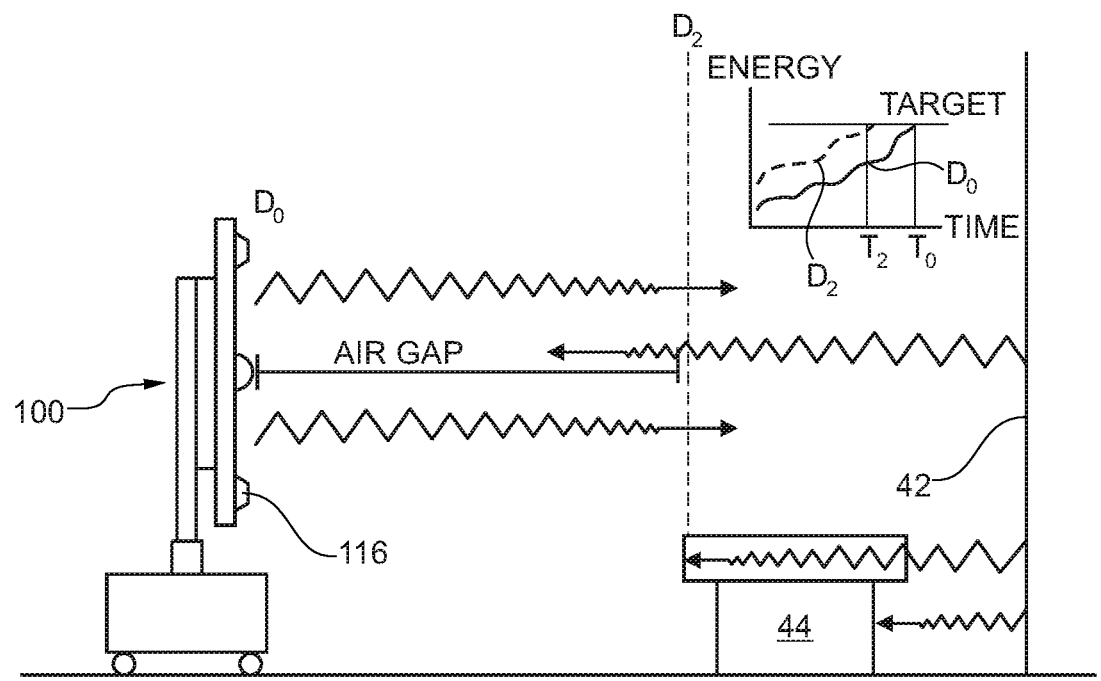

Referring now to FIG. 5, a functional illustration of an air gap compensation calculation by UV-C disinfection apparatus 100 is shown. According to an embodiment, ranging sensor 116 measures the distance from UV-C disinfection apparatus 100, $D_0$, to the target surface, $D_1$, and to the leading surface of the closest object in the room, $D_2$. The distance $D_2$ defines the air gap between the UV-C sensors 114 and the leading surface of the closest object in the room 44. The back side of object 44, i.e. the "dark" side of the object relative to UV-C disinfection apparatus 100, is disinfected by receiving UV-C radiation reflected back from the target surface 42. As discussed above, a kill dose is measured by the amount of radiation reflected from the target surface 42 to UV-C sensors 114. The kill dose is measured using reflected radiation, rather than direct energy, in order to ensure that the dark side of surfaces in the target room (i.e. surfaces not receiving direct exposure of UV-C radiation) are sufficiently disinfected. The amount of reflected radiation only needs to be measured from the leading edge of the closest object in the room 44 to measure a kill dose on the dark side of object 44. The space between $D_0$ and $D_2$ represents the air gap between UV-C sensors 114 and the leading edge of the closest object in the room 44. The intensity of the reflected radiation is reduced between $D_2$ and $D_0$, as the intensity of radiation diminishes with distance. Therefore, measuring a kill dose at $D_0$ results in an over measurement of radiation, which in turn results in overexposure UV-C radiation and increased time for UV-C disinfection apparatus 100 to complete a disinfection cycle. UV-C disinfection apparatus 100 mitigates over-exposure and minimizes disinfection time by virtually relocating UV-C sensors 114 to distance D2 by executing an air gap compensation algorithm. This enables UV-C disinfection apparatus 100 to measure the minimum required amount of reflected UV-C radiation necessary for an effective kill dose.

Figure 6:
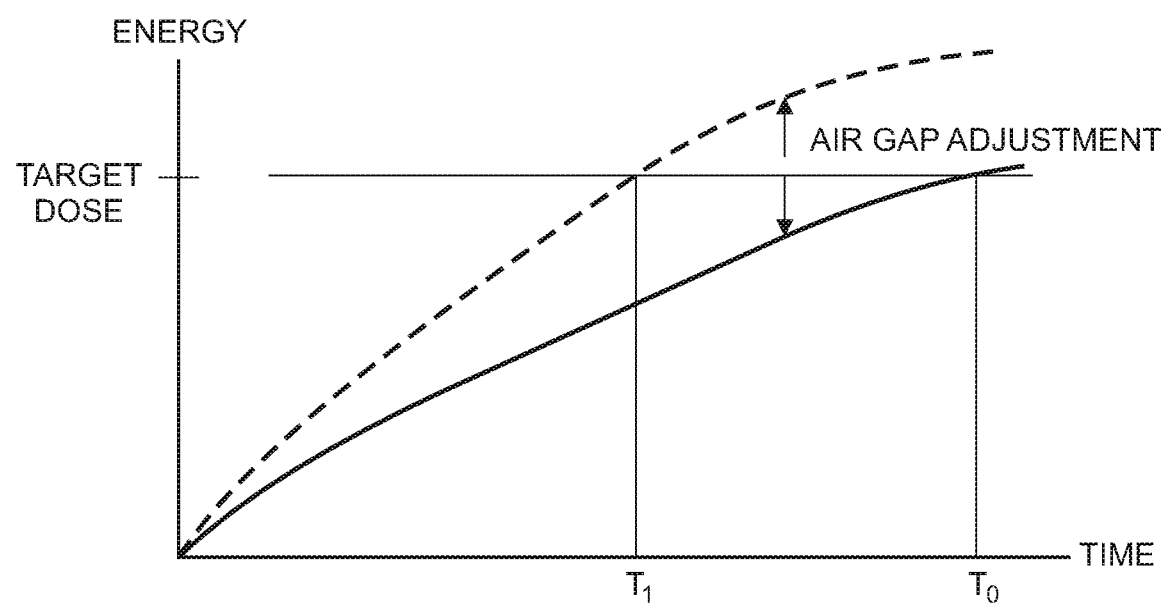
FIG. 6 is an illustration of target dose calculation, as calculated with and without compensation for air gap.

FIG. 6 further illustrates the above concepts of FIG. 5 by plotting the reflected energy received by UV-C sensors 114 (on the y-axis) as a function of time (on the x-axis) in order to reach a target dose of reflected energy. Where UV-C sensors 114 have not been virtually relocated to compensate for air gap, the time required to reach an effective kill dose is shown on the graph as $T_0$. Where UV-C sensors 114 have been virtually relocated to compensate for air gap, the time required to reach an effective kill dose is shown on the graph as $T_1$. The delta between $T_0$ and $T_1$ represents the amount of time saved during the disinfection cycle when compensating for air gap between the UV-C sensor and the location of the nearest object in the zone.

Figure 7:
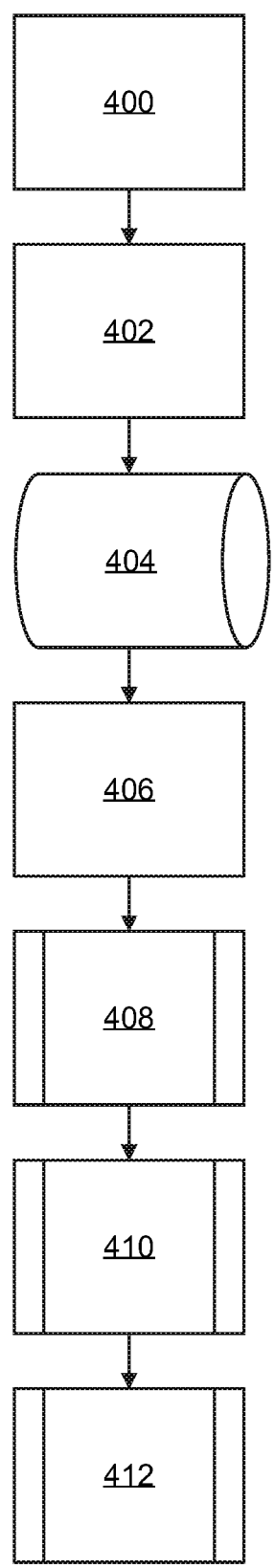
FIG. 7 is a process flow diagram of a room disinfection using a portable UV-C disinfection system, according to an embodiment.

Referring now to FIG. 7, a process flow diagram of a room disinfection using a portable UV-C disinfection system is shown. According to an embodiment, the portable UV-C disinfection system identifies the room 400 by receiving an identification tag, such as an RFID label, or other location information, such as GPS, and stores this room ID in memory 402. The room ID is communicated to a remote interface and through a network to a hospital database 404. A user positions the portable UV-C disinfection system in a room 406 and sends a command to the portable UV-C disinfection system via a remote interface to begin the disinfection cycle 408. The portable UV-C disinfection system verifies no occupants are present in the room 410, and once safety has been verified, the UV-C disinfection system begins the disinfection cycle 412.

Figure 8:
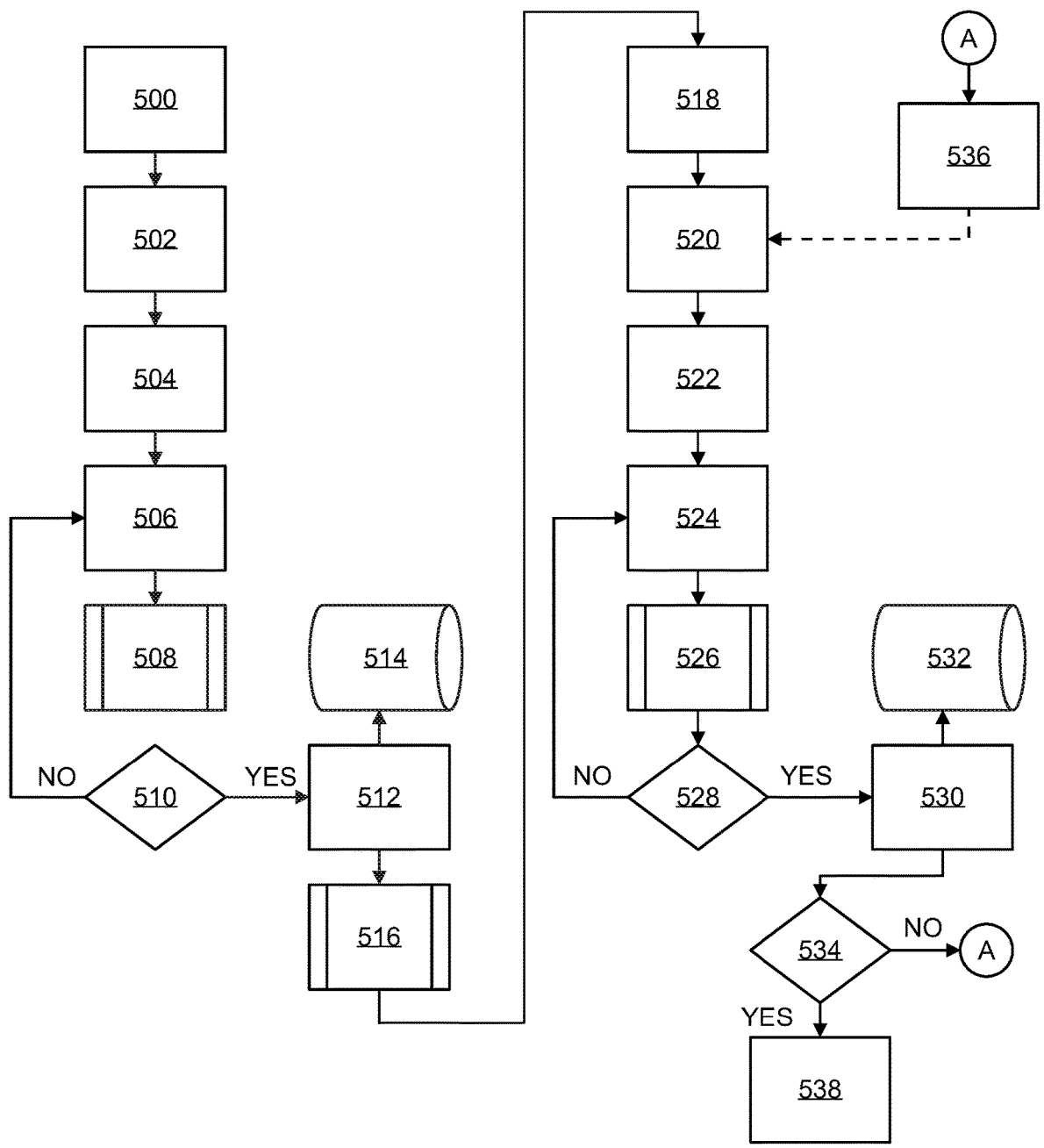
FIG. 8 is a process flow diagram of a zone disinfection by a portable UV-C disinfection system, according to an embodiment.

Referring now to FIG. 8, a flow diagram of a zone disinfection by a portable UV-C disinfection system is shown. According to an embodiment, the portable UV-C disinfection system signals the ranging to scan Zone 1 500, and calculates the distance between a UV-C sensor and the nearest object in the zone to determine air gap compensation 502 for the UV-C sensor. The UV-C emitters deliver radiation to Zone 1 504 in dual wavelengths of about 265 nm and about 405 nm. The UV-C sensors receive reflected radiation 506 from the target zone to continuously measure dosage 508. As the sensors receive reflected UV-C radiation, a decision is made as to whether or not the calculated dosage strength for a zone has been met 510, i.e. a kill dose has been administered. If "NO," the UV-C sensors continue to monitor radiation 506 and radiation is delivered until the calculated dosage for the zone has been achieved. Once the sensors receive a threshold radiation value, the UV-C emitters discontinue radiation and Zone 1 disinfection is concluded 512. The UV-C disinfection system stores dosage data in memory 514 along with room identifying information. Upon completion of Zone 1 disinfection, the array rotates to Zone 2 516.

Ranging sensors scan Zone 2 518 and calculate the distance between the UV-C sensor and the nearest object in the zone to determine air gap compensation 520 for the UV-C sensor. Alternatively, a predetermined air gap compensation parameter may be calibrated in the system. The UV-C emitters deliver radiation to Zone 2 522 in dual wavelengths of about 265 nm and about 405 nm. The UV-C sensors receive reflected radiation 524 from the target zone to continuously measure dosage 526. As the sensors receive reflected UV-C radiation, a decision is made as to whether a kill dose for the zone has been delivered 528. If "NO," the UV-C sensors continue to receive reflected radiation 524 from the target zone to continuously measure dosage 526. If "YES," the sensors have received a threshold radiation value, the UV-C emitters discontinue radiation and Zone 2 disinfection is concluded 530. The UV-C disinfection system stores dosage data in memory 532 along with room identifying information.

Upon the completion of a zone disinfection, the system processing ranging and orientation data from sensors to determine if the 360-degree rotation is complete 534. If "NO," sensors begin to scan the next successive zone until an $N^{th}$ number of zones are radiated and the cycle is complete 536. If the information from the ranging and orientation sensors indicate a complete rotation of 360 degrees and disinfection of all zones, then the cycle is complete 538. Once a disinfection cycle is complete, the portable UV-C disinfection system signals the remote interface of the completion and stores system data related to the disinfection in the device database.

Figure 9:
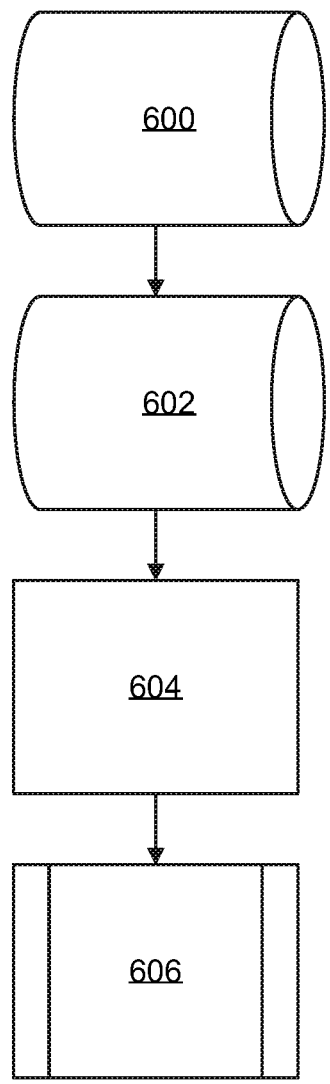
FIG. 9 is a process flow diagram of the utilization of data from a zone disinfection by a portable UV-C disinfection system, according to an embodiment.

FIG. 9 illustrates the utilization of data from a zone disinfection by a portable UV-C disinfection system. According to an embodiment, the portable UV-C disinfection system receives data from the UV-C, ranging, and orientation sensors. This data provides information as to the orientation of objects in a room and the time and dosage strength needed to disinfect a room. The data is stored in the portable UV-C disinfection system memory 600. The data is time-stamped to keep a record of when a room was disinfected 602. This time-stamped data is then communicated via a network to a hospital server 604. The received time-stamped information is then associated with a room identification and stored in a hospital database 606. This information can be utilized by quality control to determine the health of the hospital, as well as monitor the health and status of a facility wide deployment.

Figure 10:
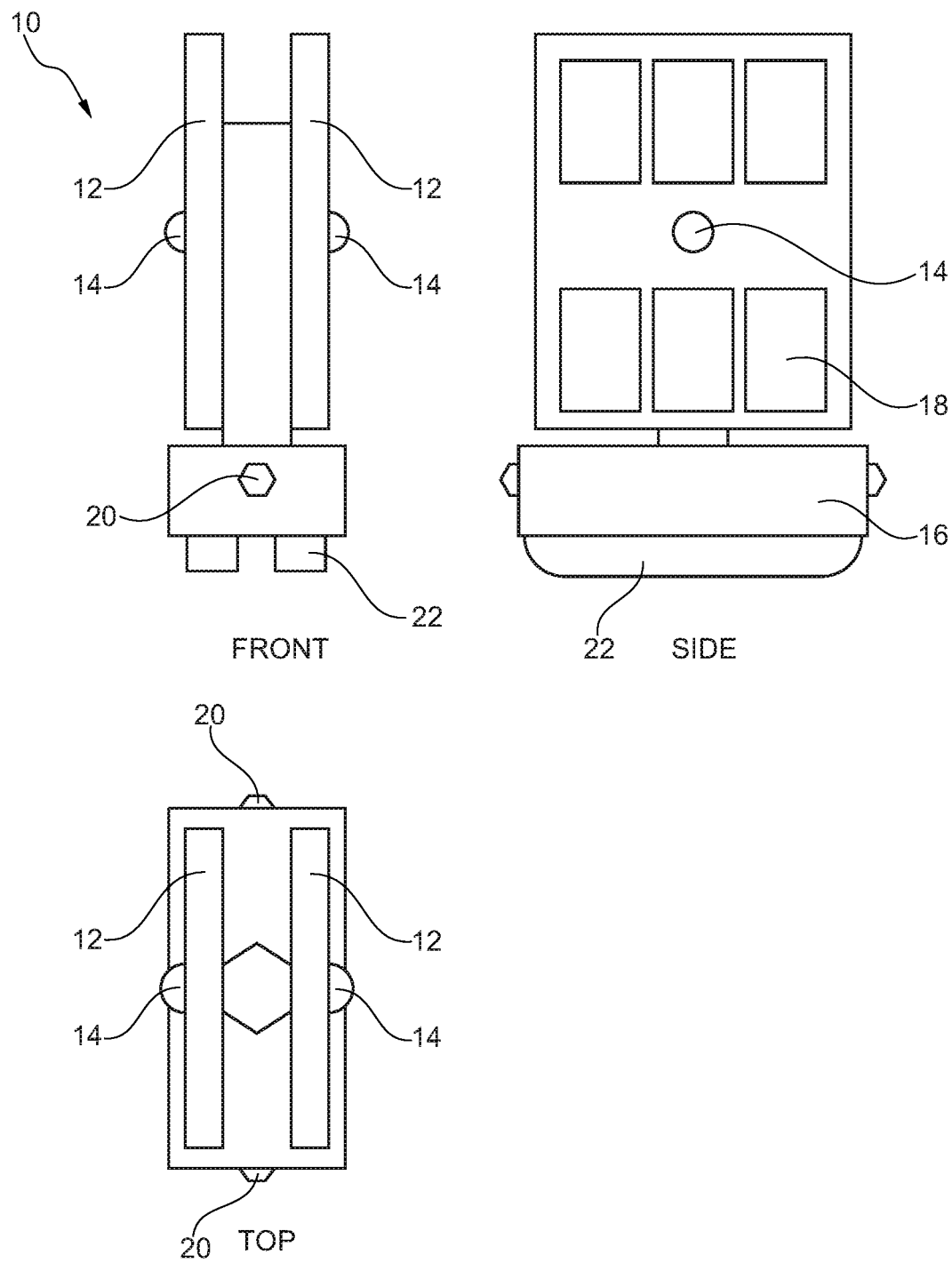
FIG. 10 is a front, side, and top view of an alternative embodiment of a portable UV-C disinfection system; and, FIG. 11 is a functional diagram of disinfection of the interior of an aircraft, according to an embodiment.
Figure 11:
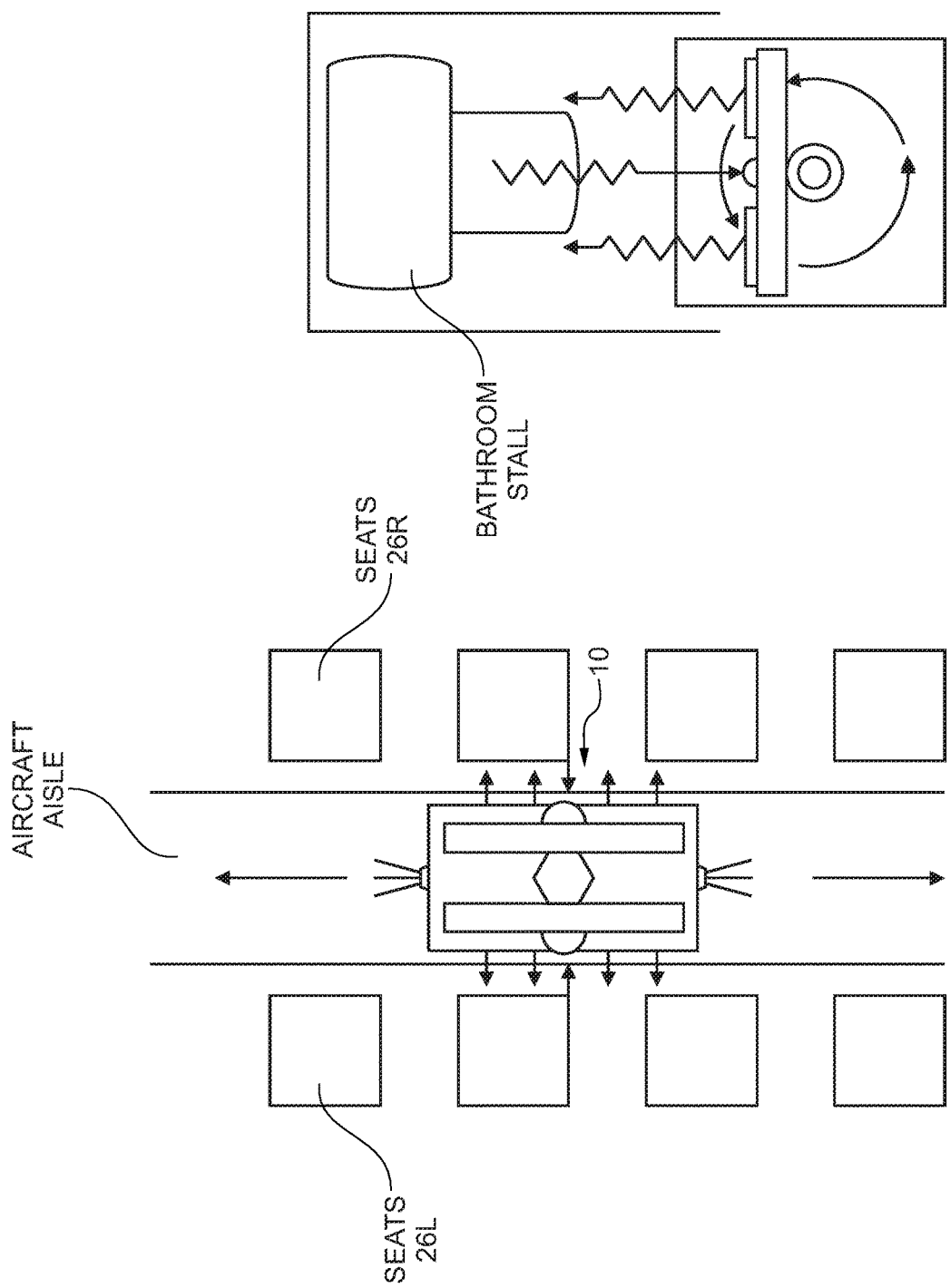

Referring now to FIG. 10, a front, side, and top view of an alternative embodiment of a portable UV-C disinfection system is shown. According to an embodiment, a UV-C disinfection apparatus 10 is generally comprised of a left and a right array surface 12, a left and a right UV-C sensor 14, a front and a rear proximity sensor 20, a base housing 16, a left and a right emitter array 18, and tracks 22. UV-C disinfection apparatus 10 may function to emit UV-C radiation in substantially the same way as described in FIG. 1 above, including the application of dual band radiation. As opposed to rotating in a 360-degree range of motion as described above, UV-C disinfection apparatus 10 emits radiation in a fixed transmission pattern from left and right array surface 12. As shown in FIG. 11, UV-C disinfection apparatus 10 is operable to disinfect the interior of an aircraft by moving down an aircraft aisle 24 using tracks 22. Left emitter array 18 delivers radiation to left seats 26L, and right emitter array 18 delivers radiation to right seats 26R. Left and right UV-C sensors 14 measure the amount of reflected energy received from left emitter array and right emitter array 18, respectively. Once a kill dose has been measured for a target zone in the aircraft, UV-C disinfection apparatus 10 continues down aircraft aisle 24 using tracks 22. Front and rear proximity sensors 20 prevent UV-C disinfection apparatus 10 from making contact with objects in its path.

Other alternative embodiments of the present disclosure may provide for one or more fixed planar emitters or one or more rotational planar emitters. The configuration of fixed vs. planar emitters may depend on the desired disinfection application. For example, the hospital room application as discussed above employs a rotational planar emitter to reduce time disinfection time and overexposure of UV radiation; while an aircraft application employs multiple fixed planar emitters. A bathroom stall, by comparison, may employ a fixed or a rotational planar emitter. Embodiments of the present disclosure provide for application-specific programming of disinfection zones; for example, "keep out" zones and target zones.

The present disclosure includes that contained in the appended claims as well as that of the foregoing description. Although this invention has been described in its exemplary forms with a certain degree of particularity, it is understood that the present disclosure has been made only by way of example and numerous changes in the details of construction and combination and arrangement of parts may be employed without departing from the spirit and scope of the invention.

What is claimed is:

1. A portable UV-C disinfection apparatus comprising:
   an array housing having a substantially planar array surface;
   a plurality of emitters coupled to the substantially planar array surface in a linear and substantially vertical configuration in relation to each other, the plurality of emitters comprising:
      at least one UV-C emitter configured to emit UV-C radiation at a wavelength of 265 nanometers, and
      at least one near-UV emitter configured to emit near-UV radiation at a wavelength of 405 nanometers;
   at least one UV-C sensor coupled to the substantially planar array surface, the at least one UV-C sensor being a closed loop sensor;
   a base housing, the base housing defining an interior portion;
   a motor housed in the interior portion of the base housing, wherein the array housing is coupled to a shaft of the motor at a bottom portion of the array housing;
   at least one ranging sensor coupled to the substantially planar array surface;
   at least one orientation sensor;
   a controller operably engaged with the motor, the plurality of emitters, the at least one UV-C sensor, the at least one ranging sensor, and the at least one orientation sensor, wherein the controller comprises a processor and at least one non-transitory computer readable medium having instructions stored thereon to cause the processor to perform one or more actions, the one or more actions comprising:
      receiving an input from the at least one UV-C sensor, the at least one ranging sensor, and the at least one orientation sensor;
      determining an amount of reflected radiation received by the at least one UV-C sensor;
      calculating an air gap compensation based on distance to a nearest object as defined by the at least one ranging sensor; and
      virtually relocating the at least one UV-C sensor to the nearest object; and,
   a battery pack housed in the interior portion of the base housing, the battery pack being operably engaged with the motor, the controller, the plurality of emitters, and the at least one UV-C sensor.

2. The portable UV-C disinfection apparatus of claim 1, further comprising a slip ring operably coupled to the bottom portion of the array housing and the shaft of the motor.

3. The portable UV-C disinfection apparatus of claim 1, wherein the plurality of emitters are selected from the group consisting of LEDs, electronic gas-discharge lamps, CFL lamps, and halogen lamps.

4. The portable UV-C disinfection apparatus of claim 1, wherein the controller is operable to modulate the motor in response to a data input from the at least one UV-C sensor and the at least one orientation sensor.

5. The portable UV-C disinfection apparatus of claim 1, wherein the controller is configured to modulate an intensity level of the at least one UV-C emitter in response to a data input from the at least one UV-C sensor and the at least one orientation sensor.

6. The portable UV-C disinfection apparatus of claim 2, wherein the motor is configured to rotate the array housing in a 360-degree range of motion.

7. A system for room disinfection using UV-C radiation comprising:
   at least one portable UV-C disinfection apparatus, the at least one portable UV-C disinfection apparatus comprising:
      an array housing having a substantially planar array surface;
      a plurality of emitters coupled to the substantially planar array surface in a linear and substantially vertical configuration in relation to each other, the plurality of emitters comprising at least one UV-C emitter configured to emit UV-C radiation at a wavelength of 265 nanometers and at least one near-UV emitter configured to emit near-UV radiation at a wavelength of 405 nanometers, the at least one UV-C emitter and the at least one near-UV emitter being configured to pulse UV-C and near-UV radiation in-phase and out of phase;
      at least one UV-C sensor coupled to the substantially planar array surface, the at least one UV-C sensor being a closed loop sensor;
      a base housing, the base housing defining an interior portion;
      a motor housed in the interior portion of the base housing, wherein the array housing is coupled to a shaft of the motor at a bottom portion of the array housing;

at least one ranging sensor coupled to the substantially planar array surface;
at least one orientation sensor;
a controller operably engaged with the motor, the plurality of emitters, the at least one UV-C sensor, the at least one ranging sensor, and the at least one orientation sensor, wherein the controller comprises a processor and at least one non-transitory computer readable medium having instructions stored thereon to cause the processor to perform one or more actions, the one or more actions comprising:
receiving an input from the at least one UV-C sensor, the at least one ranging sensor, and the at least one orientation sensor;
determining an amount of radiation received by the at least one UV-C sensor;
calculating an air gap compensation parameter based on a distance to a nearest object as defined by the at least one ranging sensor;
virtually relocating the at least one UV-C sensor to the nearest object; and
a battery pack housed in the base housing, the battery pack being operably engaged with the motor, the controller, the plurality of emitters, and the at least one UV-C sensor;
a remote system interface communicably engaged with the controller of the at least one portable UV-C disinfection apparatus; and,
a database, the database being communicably engaged with the controller of the at least one portable UV-C disinfection apparatus and the remote system interface.

8. The system for room disinfection using UV-C radiation of claim 7, wherein the remote system interface is a tablet computer or a smart phone.

9. The system for room disinfection using UV-C radiation of claim 7, wherein the controller is operable to modulate the motor in response to a data input from the at least one UV-C sensor and the at least one orientation sensor.

10. The system for room disinfection using UV-C radiation of claim 7, wherein the controller is operable to modulate an intensity level of the plurality of emitters in response to a data input from the at least one UV-C sensor and the at least one orientation sensor.

11. The system for room disinfection using UV-C radiation of claim 7, wherein the motor is operable to rotate the array housing in a 360-degree range of motion.

12. The system for room disinfection using UV-C radiation of claim 7, wherein the database is configured to store a disinfection status and a disinfection log associated across a plurality of individually identified rooms.

13. The portable UV-C disinfection apparatus of claim 1, further comprising a lens assembly protecting the plurality of emitters, the lens assembly being configured to dissipate heat from the plurality of emitters and direct radiation in a desired angle.

14. A method for room disinfection using the portable UV-C disinfection apparatus of claim 1, wherein the instructions stored on the non-transitory computer readable medium of the controller further cause the processor to measure a kill dose according to the amount of reflected radiation received by the at least one UV-C sensor and at least one kill parameter stored in a memory of the non-transitory computer readable medium.

15. The system for room disinfection using UV-C radiation of claim 7, wherein the instructions stored on the non-transitory computer readable medium of the controller further cause the processor to measure a kill dose according to the amount of reflected radiation received by the at least one UV-C sensor and at least one kill parameter stored in a memory of the non-transitory computer readable medium.

* * * * *